United States Patent [19]

Wilmore

[11] Patent Number: 5,248,697
[45] Date of Patent: Sep. 28, 1993

[54] ENHANCEMENT OF GLUTATHIONE LEVELS WITH GLUTAMINE

[75] Inventor: Douglas W. Wilmore, Brookline, Mass.

[73] Assignee: Brigham and Women's Hospital, Boston, Mass.

[21] Appl. No.: 585,846

[22] Filed: Sep. 20, 1990

[51] Int. Cl.⁵ .................................... A61K 31/195
[52] U.S. Cl. ...................................... 514/563
[58] Field of Search ......................... 514/563

[56] References Cited

U.S. PATENT DOCUMENTS 4,438,124  3/1984  Meister et al. ............... 424/270
4,439,448  3/1984  Munakata et al. ............ 424/309

OTHER PUBLICATIONS

Chemical Abstracts 96:210715v (1982).
Chemical Abstracts 100:180128n (1984).
Welbourne et al., *Life Sciences* 30:793–801 (1982).
Yamada, *Jap. J. Anesth.* 26:640–645 (1977).
Zimmerman et al., *J. Immunol.* 142(4):1405–1409 (1989).
Anderson et al., *Arch. Biochem. Biophys.* 239(2):538–548 (1985).
Babson et al., *Biochem Pharmacol.* 30(16):2299–2304 (1981).
Beck et al., *Proc. Soc. Expt. Biol.* 86:823–827 (1954).
Beck et al., *Proc. Soc. Expt. Biol.* 81:291–294 (1952).
Chen et al., *Biochem. Biophys. Res. Comm.* 151(2):844–850 (1988).
Cho et al., *J. Nutr.* 111:914–922 (1981).
Cook et al., *Biochim. et Biophy. Acta* 884:207–210 (1986).
Daas et al., *Life Sciences* 38(14):1305–1308 (1986).
Davis et al., *Current Surgery* Sep.-Oct. 1988 pp. 392–395.
Dawson et al., *Arch. Toxicol.* 55:11–15 (1984).
Deneke et al., *J. Appl. Physiol.: Respirat. Environ. Exercise Physiol.* 54(1):147–151 (1983).
Deneke et al., *J. Appl. Physiol.* 58(2):571–574 (1985).
Galvin et al., *Am. J. Physiol.* 235(6):H657–H663 (1978).
Griffith et al., *Proc. Natl. Acad. Sci. USA* 76(12):6319–6322 (1979).
Griffith et al., *Proc. Natl. Acad. Sci. USA* 76(11):5606–5610 (1979).
Harlan et al., *J. Clin. Invest.* 73:706–713 (1984).
Harrison et al., *The Lancet* 335:1572–1573 (1990).
Hirota et al., *Gastroenterology* 97:853–859 (1989).
Horejsi et al., *Folia Haematol.* 86:220–225 (1966).
Izard et al., *Mutation Research* 47:115–138 (1978).
Keller et al., *Arch. Surg.* 120:941–945 (1985).
Kern et al., *Exp. Eye Res.* 17:455–462 (1973).
Kosower, *Int. Rev. Cytology* 54:109–160 (1978).
Kosugi et al., "New Approaches To Shock Therapy:Reduced Glutathione (GSH(" in *Molecular Aspects of Shock and Trauma*, pp. 253–269, Alan R. Liss, Inc. (1983).
Lash et al., *Proc. Natl. Acad. Sci. USA* 83:4641–4645 (1986).
Lauterburg et al., *J. Clin. Invest.* 67:1415–1424 (1981).
Schulman et al., *Annals of Internal Med.* 93:330–346 (1980).

(List continued on next page.)

*Primary Examiner*—Leonard Schenkman
*Attorney, Agent, or Firm*—Sterne, Kessler, Goldstein & Fox

[57] ABSTRACT

A method of maintaining and/or enhancing tissue or plasma levels of glutathione is provided. Treatment of a mammal with a supranormal amount of glutamine, or a glutamine equivalent, prevents the reduction in tissue glutathione levels associated with exposure of the mammal to a compound capable of oxidative injury to the tissue. Such compounds may be drugs such as chemotherapeutic agents. Administration of a supranormal amount of glutamine or a glutamine equivalent after exposure of a mammal to a compound capable of oxidative injury to the tissue can ameliorate or prevent injury. Treatment of a mammal with glutamine or a glutamine equivalent can also reduce or prevent starvation- or radiation-associated oxidative damage in the tissues.

26 Claims, 1 Drawing Sheet

OTHER PUBLICATIONS

Lautersburg et al., *Gastroenterology* 77(5):A24 (1979).
Lauterburg, et al., *Adv. Exp. Med. Biol.* 136 (part A):453-461 (1981).
Leaf et al., *Biochem. J.* 41:280-287 (1947).
Lewis et al., *Pharmacology* 39:121-128 (1989).
McIntyre et al., *Int. J. Biochem.* 12:545-551 (1980).
Matthews et al., *Immunology* 62:153-155 (1987).
Meister et al., *Ann. Rev. Biochem.* 45:959-604 (1976).
Meister, *Nutrition Reviews* 42(12):397-409 (1984).
eister, *J. Biol. Chem.* 263(33):17205-17208 (1988).
Meredith et al., *Brit. Med. J.* 293:345-346 (1986).
Ogasawara et al., *Res. Exp. Med.* 189:195-204 (1989).
Richman et al., *J. Biol. Chem.* 250(4):1422-1426 (1975).
Roos et al., *Agents and Actions* 10(6):528-535 (1980).
Strubelt et al., *Toxicology and Applied Pharmacology* 60:66-77 (1981).
Sumida et al., *Jap. Cir. J.* 45:1364-1368 (1981).
Szabo et al., *Science* 214:200-202 (1981).
Szymanski et al., *P.S.E.B.M.* 129:966-968 (1968).
Waelsch et al., *J. Biol. Chem.* 144:53-58 (1942).
Watanabe et al., *Immunopharmacology and Immunotoxicology* 10(1):109-116 (1988).
Weinberg et al., *J. Clin. Invest.* 80:1446-1454 (1987).
Welbourne, *Can. J. Biochem.* 57:233-237 (1979).
Palekar et al., *Biochem. Biophys Res. Comm.* 62(3):651-657 (1975).
Ballatori et al., *Am. J. Physiol.* 263:G617-G624 (1992).

ENHANCEMENT OF GLUTATHIONE LEVELS WITH GLUTAMINE

FIELD OF THE INVENTION

The present invention is related to the maintenance and enhancement of glutathione levels in mammalian tissue and plasma.

BACKGROUND OF THE INVENTION

Glutathione is a tripeptide, L-γ-glutamyl-L-cysteinylglycine, present in high concentrations in most cell types. By virtue of its reactive sulfhydryl group, glutathione is able to donate a hydrogen ion and unpaired electron and neutralize peroxides and free radicals (Meister, A., *Nutrition Reviews* 42:397-410 (1984); Meister, A., *J. Biol. Chem.* 263:17205-17208 (1988); Kosower et al., *Int. Rev. Cytology* 54:109-160 (1978)).

Experimental data demonstrate that glutathione and its redox system enzymes, glutathione peroxidase and reductase, provide a widespread and essential protection system from both endogenous and exogenous oxidative assault. In numerous cell types, normal or enhanced levels of glutathione are protective against cellular injury induced by a variety of different agents (Harlan et al., *J. Clin. Invest.* 73:706-713 (1984); Roos et al., *Agents and Actions* 10:528-535 (1980); Weinberg et al., *J. Clin. Invest.* 80:1446-1454 (1987); Babson et al., *Biochem. Pharm.* 30:2299-2304 (1981); Lash et al., *Proc. Natl. Acad. Sci. USA* 83:4641-4645 (1986); Szabo et al., *Science* 214:200-202 (1981)). Conversely, depletion of glutathione has been demonstrated to sensitize tissues to increased oxidative injury by various stresses (Deneke et al., *J. Appl. Physiol.* 58:571-574 (1985); Davis et al., *Current Surgery* 45:392-395 (1988); Chen et al., *Biochem. Biophys. Res. Comm.* 151:844-850 (1988)).

Glutathione synthesis is directed by the sequential activities of γ-glutamylcysteine synthetase (GGCS) and glutathione synthetase. GGCS is the rate limiting enzyme, and is feedback inhibited by intracellular glutathione levels. In addition, the rate of synthesis can be regulated by substrate availability. It has been reported that cysteine is rate-limiting for glutathione synthesis. (Meister, A., *Nutrition Reviews* 42:397-410 (1984); Richman et al., *J. Biol. Chem.* 250:1422-1426 (1975)).

Degradation of glutathione is dependent upon γ-glutamyl transpeptidase (GGTP), a membrane bound enzyme, which catalyzes the transfer of the γ-glutamyl group of glutathione to an acceptor molecule, either an amino acid or water, to form a γ-glutamyl amino acid or glutamate respectively. The cysteine-glycine moiety of the degraded glutathione is quickly broken down by a dipeptidase and each amino acid is absorbed intracellularly. The γ-glutamy amino acid is translocated into the cell and acted upon by γ-glutamyl cyclotransferase to form the free amino acid and oxoproline. Oxoproline (pyroglutamic acid) is converted to glutamate by 5-oxoprolinase. Glutamate can then be used for glutathione synthesis to complete the cycle (Meister, A., *Nutrition Reviews* 42:397-410 (1984)).

The γ-glutamyl cycle has been shown to exist in many cell types, but its precise physiologic function is not well understood. It has been proposed that the formation of γ-glutamyl amino acid constitutes one form of an amino acid transport mechanism (Griffith et al., *Proc. Natl. Acad. Sci. USA* 76:6319-6322 (1979)). However, others have noted that under physiologic conditions, the hydrolysis of the γ-glutamyl complex with the formation of glutamate is the dominant reaction (McIntyre et al., *Int. J. Biochem.* 12:545-551 (1980); Cook et al., *Biochim. Biophys. Acta* 884:207-210 (1986)).

It has been reported that toxic doses of endotoxin in mice significantly decreased the concentration of non-protein bound sulfhydryl groups, of which glutathione comprised ninety percent. It was demonstrated that scalding, hind leg ligation, endotoxin administration, exposure to cold, tumbling trauma, and severe hemorrhage all resulted in significant decreases in liver glutathione levels. The mechanism of this depletion and its significance were not understood (Beck et al., *Proc. Soc. Expt. Biol.* 81:291-294 (1952); Beck et al., *Proc. Soc. Expt. Biol.* 86:823-827 (1954)).

Following the observations of Beck et al., other investigators examined the effects of glutathione in a number of animal shock models. The exogenous administration of glutathione to animals in endotoxic shock, (Szymanski et al., *Proc. Soc. Expt. Biol.* 129:966-968 (1968); Sumida et al., *Jap. Circ. J.* 45:1364-1368 (1981); Kosugi et al., "New Approaches to Shock Therapy: Reduced GSH," in *Molecular Aspects of Shock and Trauma*, A. M. Lefer, ed., Alan R. Liss, Inc., New York (1983)), hemorrhagic shock (Horejsi et al., *Folia Haematol.* 86:220-225 (1966); Yamada, H., *Jap. J. Anesth.* 26:640-645 (1977)), and cardiogenic shock (Galvin et al., *Am. J. Physiol.* 235:H657-H663 (1978)), significantly attenuated tissue injury and improved survival. In addition, recent evidence has demonstrated that tumor necrosis factor may induce cell damage by oxidative injury (Watanabe et al., *Immunopharm. Immunotox.* 10:109-116 (1988); Matthews et al., *Immunology* 62:153-155 (1987)), and that in rats, depletion of glutathione levels enhanced mortality to previously nonlethal doses of tumor necrosis factor (Zimmerman et al., *J. Immunology* 142:1405-1409 (1989)).

Intestinal mucosal levels of glutathione have also been shown to decrease significantly after 24 to 48 hours of starvation (Ogasawara et al., *Res. Exp. Med.* 189:195-204 (1989); Siegers et al., *Pharmacology* 39:121-128 (1989)). Erythrocyte glutathione levels do not change during this period of starvation, consistent with the longer, four day, intracellular half-life (Cho et al., *J. Nutr.* 111:914-922 (1981)).

Radiation therapy is a regional form of treatment for control of localized cancers. Success of radiotherapy depends upon the production of free radicals by the ionizing events following irradiation. The resulting free radicals and oxidizing agents produce DNA strand breaks and other damage to DNA molecules in the localized cancer. However, radiotherapy is associated with accompanying damage to normal tissues as well, and damage to normal tissues increases with the size of the tumor. Prevention or reduction of the oxidative damage to normal tissue would be of benefit to a patient receiving radiotherapy.

Many therapeutic substances can cause liver damage by virtue of the production of oxidative metabolites. Acetaminophen (paracetamol) is a commonly used over-the-counter analgesic preparation, and a frequent cause of poisoning. A metabolic route of acetaminophen is a cytochrome P-450 catalyzed activation which results in the formation of a reactive metabolite that binds to cellular nucleophiles, particularly reduced glutathione.

Another common substance which can cause oxidative damage to the liver is acrolein, a metabolite of the widely used anticancer drug cyclophosphamide. Acrolein binds to cellular sulfhydryls and can deplete intracellular glutathione, leading to cell death. (Dawson, J. R. et al., *Arch. Toxicol.* 55:11-15 (1984)). The early clinical manifestations of cyclophosphamide toxicity include hemorrhagic cystitis, sterility, and alopecia. (Izard, C. et al.. *Mutation Research* 47:115-138 (1978)).

Compounds capable of causing oxidative damage are not limited to intentionally administered pharmaceuticals. Paraquat is an herbicide which has toxic effects on most organs including the lungs, liver, heart, gastrointestinal tract and kidneys. Paraquat undergoes a redox cycling reaction which can lead to the production of reactive oxygen species, including hydrogen peroxide and the superoxide radical. (Dawson, J. R. et al., *Mutation Research* 47:115-138 (1978)).

N-acetylcysteine has a protective effect against the toxicity of acetaminophen, acrolein and paraquat in isolated hepatocytes. Acting as a precursor for glutathione, N-acetylcysteine decreased the toxicity of paraquat co-incubated with hepatocytes. (Dawson, J. R. et al., *Arch. Tox.* 55:11-15 (1984)). N-acetylcysteine is currently a clinical treatment of choice for patients who have ingested excess amounts of acetaminophen. However, N-acetylcysteine is not approved for intravenous use in the United States, and is thus not available for patients presenting with compromised gastrointestinal function.

In cases of acetaminophen overdose, depletion of intracellular glutathione can lead to cell death and liver damage. (Dawson, J. R. et al., *Arch. Tox.* 55:11-15 (1984)). In Great Britain alone, over 150 people die each year as a result of acetaminophen poisoning. (Meredith, T. J. et al., *Br. Med. J.* 293:345-346 (1986)). In a study of 100 patients with acetaminophen-induced liver failure, a 37% mortality was observed despite administration of the currently used antidote, acetylcysteine. Mortality was 58% among patients not receiving the antidote. (Harrison, P. M. et al., *The Lancet:*1572-1574 (Jun. 30, 1990.)) Thus, although the currently used treatment achieves some reduction in mortality, a more effective treatment is needed to further reduce the mortality rate.

Acetaminophen, cyclophosphamide, and other drugs that can be metabolized to toxic derivatives, are often administered to patients already under significant physical stress due to illness and lack of nutrition. In these patients, the hepatic stores of glutathione may have fallen below normal levels, lowering the detoxifying capability of the liver. The effect of starvation on tissue glutathione levels is therefore important in view of the diminished nutritional status of patients receiving anticancer drugs or other potent pharmaceutical agents.

Hepatic glutathione levels fall approximately 50% within 24 to 48 hours of starvation or low protein diet (Leaf et al., *Biochem. J.* 41:280-287 (1947); Cho et al., *J. Nutr.* 111:914-922 (1981); Strubelt et al., *Toxic. Appl. Pharm.* 60:66-77 (1981)). This is consistent with the short half life of liver glutathione of approximately 4 hours. With refeeding, hepatic levels of glutathione return to normal within 24 hours. Exogenous administration of glutathione, either parenterally or intraperitoneally, is relatively ineffective in enhancing tissue levels (Anderson et al.. *Arch. Biochem. Biophys.* 239:538-548 (1985)). Plasma glutathione is rapidly metabolized, and most tissues are unable to transport large amounts of intact exogenous glutathione. The small amounts of glutathione present in plasma are due primarily to rapid hepatic synthesis and release, and to rapid renal degradation.

Although plasma levels of glutathione are 100-500 times lower than intracellular levels, a significant amount of glutathione is able to circulate because of its rapid flux (Griffith et al.. *Proc. Natl. Acad. Sci. USA* 76:5606-5610 (1979)). Hirota et al. have hypothesized that the release of plasma glutathione by the liver is important in the protection of cell membranes from oxidative damage. Shock-induced hepatic dysfunction may inhibit sufficient synthesis and release of plasma glutathione, enabling subsequent oxidative damage to occur (Hirota et al., *Gastroenterolgy* 97:853-859 (1989); Keller et al., *Arch. Surg.* 120:941-945 (1985)).

Patients unable to take in adequate nutrition are often treated with total parenteral nutrition formulas. Parenteral administration of pharmaceutical preparations is also appropriate for patients with gastrointestinal dysfunction. However, the commonly used antidote for acetaminophen overdose, N-acetylcysteine, is not approved for intravenous use in the United States. Thus, patients presenting with non-functional or dysfunctional gastrointestinal systems associated with acetaminophen overdose cannot be provided with N-acetylcysteine intravenously.

In view of the crucial role played by glutathione in detoxification of drug metabolites and in preventing peroxidation of cell components, a method for maintaining hepatic stores of glutathione, particularly during times of stress to the body, including chemotherapy, is needed.

SUMMARY OF THE INVENTION

The present invention provides a method of maintaining or enhancing tissue or blood levels of glutathione by the administration of glutamine.

BRIEF DESCRIPTION OF THE FIGURES

FIG. 1 is a graph illustrating hepatic glutathione levels in rats treated with 5-fluorouracil (5FU), and fed standard TPN or glutamine-supplemented TPN.

DESCRIPTION OF THE PREFERRED EMBODIMENTS

Figure 1:
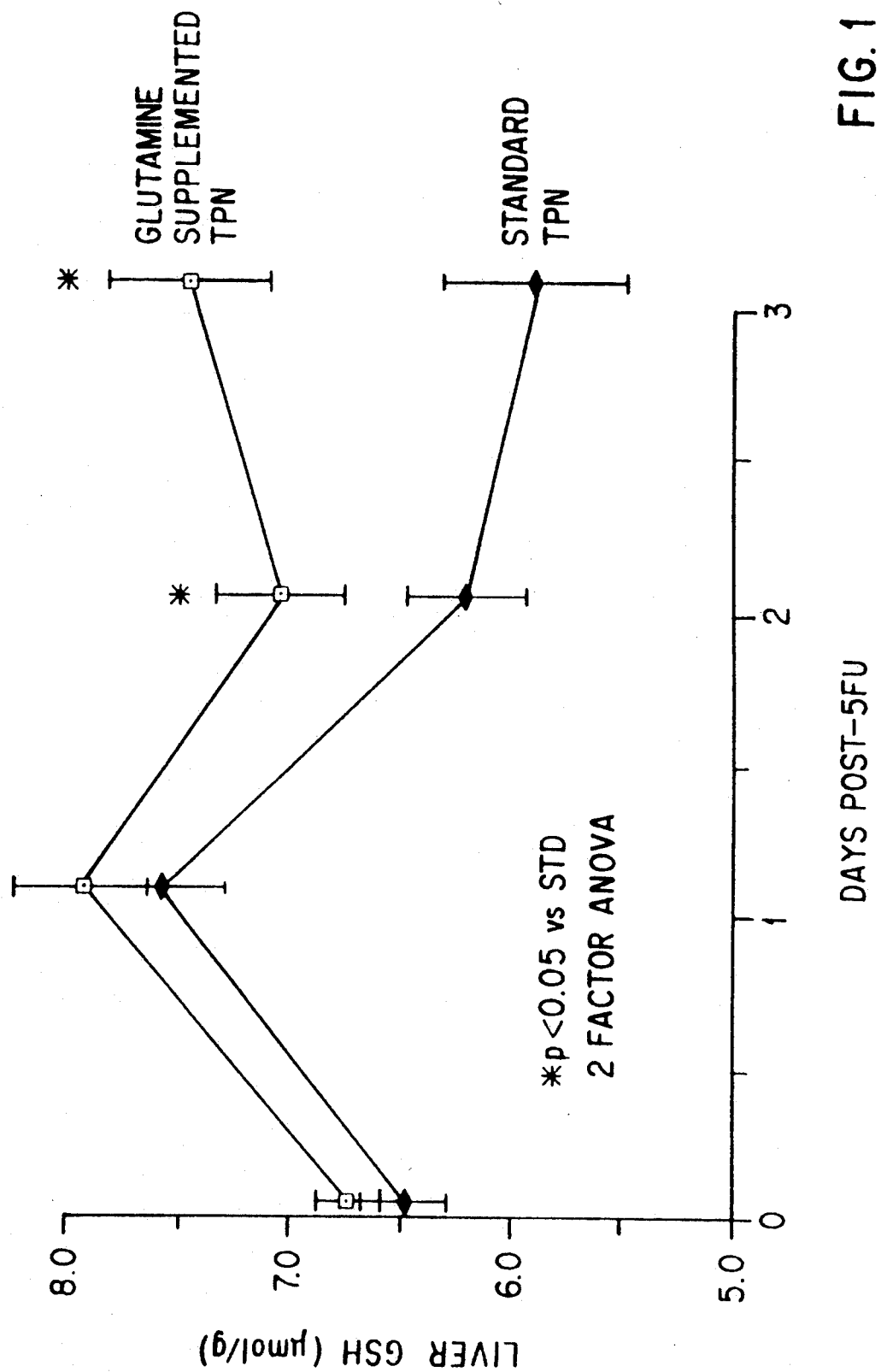
FIG. 1.

According to the methods of the invention, the levels of glutathione in the liver can be maintained or enhanced by administration of glutamine. The invention is intended to be used in all physiological and pathological conditions in which the tissue or blood glutathione levels are known or suspected to be diminished. The invention may also be used in conjunction with any therapeutic regimen likely to reduce liver glutathione levels. In addition, the invention may be used in conditions in which hepatic glutathione stores may be reduced as a result of malnutrition, either alone or in association with a pathological condition.

Maintenance of adequate concentrations of glutathione is crucial, and the liver is capable of synthesizing large amounts of glutathione at a rapid rate during stress. In the case of drug-induced tissue damage, the increased rate of glutathione synthesis is necessary to counteract the large quantities of drug-glutathione conjugates excreted in the urine after metabolism to mercapturic acid. The amount excreted can exceed by several fold the total amount of glutathione originally present in the liver.

However, a variety of conditions can deplete hepatic glutathione, leaving a smaller reserve for the detoxification functions. Fasting decreases hepatic glutathione concentrations, and oxidative stress leads to increased transport of glutathione, as disulfide, from the liver. Under conditions of increased demand on glutathione synthesis, the liver may be unable to meet additional requirements for its glutathione pool, and the administration of an otherwise non-toxic dose of a drug may lead to cell and tissue injury.

As used herein, the term "mammal" is intended to include humans.

By "glutamine equivalent" is meant an analogue, substitution product, isomer, homologue, or derivative of glutamine which can maintain or enhance the amount of glutathione in a mammalian cell or in tissue or plasma, in vitro or in vivo.

By "maintain" the amount, level or concentration of glutathione in a cell or in tissue or plasma is meant the prevention of partial or complete depletion of glutathione that would otherwise occur in the absence of treatment according to the invention.

By "enhance" the amount, level or concentration of glutathione in a cell or in tissue or plasma is meant the increase in the amount, level or concentration of glutathione over that which was present in the cell, tissue or plasma prior to treatment.

By "chemotherapeutic treatment" is meant the administration to a mammal of a drug or chemotherapeutic agent to prevent, alleviate or cure a disease or pathological condition. Commonly the chemotherapeutic agent would be administered to treat cancer, but other chemotherapeutic agents are included within the meaning of the term.

By "xenobiotic" is meant any compound to which a mammal is exposed, but which does not naturally occur in the mammal. The compound may commonly be a drug, chemotherapeutic agent, pesticide, or herbicide, but can also be any other compound which has a nucleophilic group, or which is metabolized to a derivative having a nucleophilic group.

By "supranormal amount" of glutamine is meant an amount or concentration of glutamine greater than the amount that a mammal would otherwise receive in the diet or otherwise. In relation to a human, a supranormal amount of glutamine is an amount greater than that found in the diet or otherwise provided to that human, for example as a component of a total parenteral nutritional formulation, or in a specific dietary formulation.

By "shock" is meant a partial or total decrease or cessation of blood flow in a mammal. The term includes hemorrhagic shock, septic shock, and conditions associated with cross-clamping of blood vessels during organ transplantation.

By "enteral" is meant that portion of the alimentary canal including the stomach and the portion distal to the stomach.

By "parenteral" is meant that region outside the digestive tract.

According to one aspect of the invention, a supranormal amount of glutamine or a glutamine equivalent is administered to a person who is receiving, or will receive, chemotherapy or radiation treatment for a cancerous condition. Administration of glutamine or a glutamine equivalent before, during and/or after chemotherapy or radiation treatment enhances the hepatic stores of glutathione, thereby increasing the ability of the liver to detoxify metabolites resulting from the chemotherapy or radiation treatment. The tissue-damaging effect of free radicals generated during radiation treatment can also be alleviated by this administration of glutamine or a glutamine equivalent.

Glutamine can also be administered to a person who has ingested or has been exposed to a compound likely to produce one or more toxic metabolites. For example, an overdose of acetaminophen can cause liver toxicity due to saturation of the major metabolic route for acetaminophen.

Normally, acetaminophen is removed from the body by conjugation to glucuronic acid and to sulfate, but in cases of overdose, these pathways become saturated. Excess acetaminophen is activated by cytochrome P-450, and the reactive metabolite binds to reduced glutathione. In the absence of adequate glutathione, the reactive metabolite binds to other cellular components and causes liver damage. According to the invention, administration of a supranormal amount or glutamine or a glutamine equivalent after diagnosis of acetaminophen overdose can alleviate or prevent some or all of the liver damage that would otherwise occur without glutamine administration.

The amount of glutamine or glutamine equivalent effective to maintain or enhance tissue or plasma glutathione levels will vary depending upon the needs of the patient. For a patient receiving long-term chemotherapy, it is preferable to administer the glutamine or glutamine equivalent at frequent intervals throughout the day to achieve and maintain an increased level of glutathione. Depending upon the severity of the disease, the glutamine can be administered intravenously, or can be incorporated into the diet. The amount of glutamine administered can vary from 0.1 to 2.0 grams per kilogram body weight per day, with a preferred range of 0.3 to 0.5 grams per kilogram body weight per day.

In cases of acute poisoning, such as exposure to paraquat or to any other compound that has a nucleophilic group or is metabolized to a nucleophilic derivative, it is preferable to administer a first supranormal amount of glutamine or glutamine equivalent, in the range of 0.5 to 2.0 grams per kilogram body weight, to achieve a rapid increase in the hepatic level of glutathione. After the initial treatments, further amounts of glutamine or glutamine equivalent, in the range of 70 to 500 mg per kilogram body weight per day, can be administered to maintain the glutathione levels. The route of administration will depend upon the severity of the poisoning, and an initial intravenous administration can be followed by subsequent oral doses, either alone or with food.

The administration of glutamine can be by enteral and parenteral means. Enteral administration can be accomplished by tubing placed via the nose into the gastric or duodenal regions.

Examples of parenteral administration include, but are not limited to, routes such as subcutaneous, intramuscular, or intravenous injection, nasopharyngeal or mucosal absorption, or transdermal absorption. Preparations for parenteral administration include sterile aqueous or non-aqueous solutions, suspensions and emulsions. Carriers or occlusive dressings can be used to increase skin permeability and enhance absorption.

Glutamine can be administered either alone or as a dietary supplement. When used as a dietary supplement, the glutamine can be mixed with an existing enteral or parenteral diet prior to administration to the patient. For example, glutamine can be incorporated in a standard total parenteral nutrition (TPN) formulation. Alternatively, the glutamine can be administered separately without mixing it directly with other components of the diet.

The methods of the invention can also be practiced with functional analogues, substitution products, isomers, or homologues of glutamine which retain the equivalent functional characteristics of glutamine. In particular, a glutamine equivalent would effectively maintain or enhance the level of glutathione in a hepatic cell, when tested either in vitro or in vivo.

Administration of glutamine or a glutamine equivalent protects against toxicity resulting from acetaminophen. Acetaminophen is a potent hepatotoxic agent commonly used as an analgesic, either alone or in combination with, for example, codeine or pseudoepinephrine hydrocnloride. Pharmaceutical compositions containing acetaminophen are freely available as over-the-counter products. Hepatic toxicity, sometimes fatal, is a known effect of acetaminophen overdose.

Common preparations of acetaminophen contain 325-500 mg per tablet or caplet. Hepatic toxicity can occur with ingestion of 10 grams, which is equivalent to twenty 500 mg tablets. However, fatality can occur following ingestion of 15 grams, and consumption of 100 tablets (30 to 50 grams of acetaminophen) prior to hospital admission for overdose is not unknown.

In a study of 100 patients with acetaminophen-induced fulminant hepatic failure, it was reported that mortality was 58% in patients who did not receive an acetylcysteine antidote, and 37% in patients who received the antidote 10-36 hours after the overdose. (Harrison, P. M. et al., *The Lancet:*1572-1574 (Jun. 30, 1990)).

According to the invention, administration of glutamine decreases the mortality associated with acetaminophen toxicity. Ten hours after treatment with acetaminophen, rats previously fed glutamine for five days showed a neat normal recovery of the hepatic glutathione levels, which were reduced 6 hours after treatment with acetaminophen. The hepatic level of glutathione in rats fed a normal diet were lower that the normal levels at 10 hours.

The difference in recovery of the glutathione levels was accompanied by greater mortality (46%) in the group of rats receiving a normal diet as compared with the 15% mortality of rats receiving a glutamine-supplemented diet.

Administration of supranormal amounts of glutamine to a human following ingestion of an overdose of acetaminophen is associated with maintenance of hepatic function within normal limits and recovery of the patient. Treatment with 40 grams per day of glutamine was initiated in a patient 20 hours after he ingested 32.5 grams of acetaminophen (100 325-mg caplets). The glutamine was administered intravenously, in a total of 100 grams of amino acids per day, including 1 gram or methionine. Enteral administration was not possible due to lack of function of the patient's gastrointestinal tract.

Most liver function tests were within normal limits during the four days of glutamine administration, and treatment was discontinued after four days in view of the patient's recovery. Thus, administration of supranormal amounts of glutamine according to the invention is associated with maintenance of liver function and recovery of a patient following consumption of a potentially fatal overdose of acetaminophen.

Glutamine administration also reduces the toxicity associated with another commonly used drug, 5-fluorouracil (5-fluoro-2,4 (1H, 3H)-pyrimidinedione, referred to as 5FU). 5FU is a potent chemotherapeutic agent indicated for management of carcinoma of the colon, rectum, breast, stomach and pancreas. Beginning days or weeks before administration of 5FU, the tissue levels of glutathione can be enhanced by the administration of a supranormal amount of glutamine. Glutamine administration can also be continued during 5FU therapy to maintain the enhanced glutathione levels.

In rats fed glutamine-supplemented TPN for 5 days before 5FU treatment, liver and jejunal glutathione levels were significantly higher than the levels in rats fed standard TPN. The day 3 survival rate for rats given standard TNP was 64%, but the survival rate for rats given glutamine-supplemented TPN was 88%, a significant increase over the standard TPN group.

Thus, administration of a supranormal amount of glutamine can effect a significant increase in tissue levels of glutathione, and a significant increase in survival, in rats exposed to common therapeutic agents. Furthermore, administration of a supranormal amount of glutamine is associated with survival, and maintenance of normal liver function, in a human following ingestion of a potentially fatal dose of the common hepatotoxin, acetaminophen.

The following examples further illustrate the ability of glutamine administration to enhance tissue glutathione levels and to decrease the mortality associated with exposure of mammals to agents capable of causing oxidative injury to tissues. These examples should in no way be considered limiting, but are merely illustrations of various features of the present invention.

Example 1

Male Wistar rats (n=69, 202±2 g) underwent jugular venous catheterization, and were randomized to one of two groups: (1) standard TPN (STD), and (2) glutamine supplemented TPN (Glutamine-TPN). All TPN diets were isonitrogenous and isocaloric. After 5 days of feedings, 5FU (150 mg/kg) was injected intraperitoneally. Animals were serially killed at 0 (baseline, before 5FU), 1, 2, and 3 days post 5FU administration. Tissue was harvested for determination of hepatic and jejunal mucosal glutathione, and plasma glutamine. Total glutathione was assayed by the method of Anderson (Anderson, M. E., "Enzymatic and chemical methods for the determination of glutathione," in *Glutathione,* Dolphin et al., eds, John Wiley & Sons, Inc., New York, Part A, pp. 339-365 (1989)). Additional animals were studied to obtain 72 hour survival data. Results are presented as mean ±SEM.

Baseline tissue glutathione levels were similar in both groups (FIG. 1). After 5FU administration, hepatic glutathione decreased to below normal levels in STD animals. In contrast, glutamine-TPN animals were able to maintain hepatic glutathione at significantly higher levels at 2 and 3 days post-5FU (FIG. 1). Significant survival differences between groups became apparent at these later time points. Jejunal glutathione tended to follow a similar pattern (Table 1).

The administration of glutamine-supplemented TPN resulted in the maintenance of greater hepatic and jejunal glutathione levels than observed in animals receiving standard TPN. Thus, the administration of glutamine enhances tissue glutathione levels and provides protective effects in oxidative injury.

Example 2

Following jugular venous catheterization, male Wistar rats (n=97, 201±2 g) were randomized to one of two groups: (1) glutamine-supplemented TPN (GLN), and (2) standard TPN (STD). All parenteral diets were isonitrogenous and isocaloric. On the 5th day of feeding, acetaminophen (400 mg/kg IP) was administered, and animals were killed at 0, 1, 6, 10 and 24 hours after injection. Tissue was harvested for hepatic glutathione and liver histology. Plasma was obtained for hepatic enzymes and glutathione (total and oxidized) determinations.

As shown in Table 2, animals receiving glutamine had significantly higher hepatic glutathione levels compared with STD animals at both 6 hours and 10 hours following acetaminophen administration. At 24 hours, animals receiving glutamine-supplemented TPN had significantly lower plasma hepatic enzyme levels as well as decreased mortality compared with STD animals. Plasma glutamine levels were maintained in the supplemented animals but fell below normal in the STD group.

The data indicate that the administration of glutamine-supplemented TPN results in the preservation of higher hepatic glutathione levels, greater hepatic protection, and decreased mortality during acetaminophen-induced hepatic injury. The data further indicate that enhanced survival correlates with glutamine supplementation and support of hepatic glutathione synthesis, and that administration of a glutamine-supplemented diet enhances host antioxidant defenses.

Example 3

A 48-year-old man was admitted to the Emergency Room five hours after ingestion of 100 caplets each containing 325 mg of acetaminophen, in a suicide attempt. On admission, the patient's serum level of acetaminophen was 224 mg/dL. The patient also consumed an unknown amount of barbiturates and ibuprofen. The standard therapy indicated for acetaminophen overdose, enteral administration of N-acetylcysteine, was not feasible for this patient due to gastrointestinal dysfunction.

Twelve hours after admission, intravenous administration of a 10% solution of dextrose containing glutamine and other amino acids was initiated. Over the course of four days, the patient received 40 grams of glutamine and 1 gram of methionine per day, in a total of 100 grams amino acids per day.

Most liver function tests performed were within normal limits during the four days of intravenous infusion of glutamine. As shown in Table 3, total bilirubin did not rise above normal levels during and after glutamine treatment.

Treatment was discontinued after four days, at which time the patient had made substantial recovery.

Although the present invention has been described in connection with preferred embodiments, it is understood that modifications and variations may be resorted to without departing from the spirit and scope of the invention. Such modifications are considered to be within the purview and scope of the invention and the appended claims.

TABLE 1

| Group | Liver GSH ($\mu$mol/g. wet wt) | | Jejunal GSH ($\mu$mol/g. wet wt) | | Plasma GLN ($\mu$M) | Day 3 Survival |
|---|---|---|---|---|---|---|
| | Day 2 | Day 3 | Day 2 | Day 3 | | |
| STD (n = 24) | 6.14 ± 28 | 5.83 ± 42 | 1.91 ± 14 | 1.96 ± 14 | 671 ± 30 | 64% (21/33) |
| GLN-TPN (n = 28) | 6.99 ± 29* | 7.38 ± 37* | 2.09 ± 17 | 2.27 ± 14 | 870 ± 47 | 88% (29/33)+ |

*$p<0.05$ vs STD by 2 factor ANOVA. Scheffe F-test post hoc.
+$p<0.05$ vs TPN by Chi square.

TABLE 2

| GROUP | 0 hrs | 6 hrs | 10 hrs | SGPT (IU/L) | GLN ($\mu$M) | MORTALITY |
|---|---|---|---|---|---|---|
| GLN (n = 37) | 6.68 ± .58 | 3.18 ± .31* | 6.07 ± .26* | 178 ± 16* | 660 ± 26* | 4/26 (15%)+ |
| STD (n = 35) | 6.34 ± 17 | 1.85 ± .10 | 4.15 ± 61 | 262 ± 39 | 469 ± 68 | 13/28 (46%) |

*$p<0.05$ vs. STD by 2 factor ANOVA.
+$p<0.05$ vs. STD by Chi square.

TABLE 3

| | Pretreatment | Treatment* | | | | Post-Treatment | |
|---|---|---|---|---|---|---|---|
| | Day 0 | Day 1 | Day 2 | Day 3 | Day 4 | Day 1 | Day 3 |
| Total bilirubin (normal 0.1–1.0 mg/dl | 0.5 | 0.3 | 0.5 | 0.3 | 0.5 | 0.7 | 0.4 |
| AST (normal 22–47 units/ml) | 15 | 33 | 37 | 74 | 185 | 196 | 40 |

*Indicates day after initiating treatment with glutamine.

We claim:

1. A method of enhancing the tissue or plasma concentration of glutathione in a mammal with diminished glutathione levels, said method comprising administering to said mammal an amount of glutamine, said amount being effective to enhance the tissue concentration of glutathione, wherein said diminished glutathione levels in said mammal is caused by a condition selected from the group consisting of cancer therapy, malnutrition, shock, infection, sepsis and anorexia.

2. The method of claim 1 wherein said mammal is a human.

3. The method of claim 1 wherein said glutamine is administered parenterally.

4. The method of claim 3 wherein said glutamine is administered intravenously.

5. The method of claim 1 wherein said glutamine is administered enterally.

6. The method of claim 1 wherein said shock is associated with organ transplantation.

7. The method of claim 1 wherein said shock is associated with infection.

8. A method of reducing the hepatotoxicity of a xenobiotic or a nucleophilic metabolite thereof, said method comprising administering to a mammal exposed to said xenobiotic an amount of glutamine, said amount being effective to enhance the hepatic concentration of glutathione.

9. A method of claim 8 wherein said mammal is a human.

10. A method of claim 8 wherein said xenobiotic is a chemotherapeutic agent.

11. A method of claim 8 wherein said xenobiotic is chosen from the group containing paraquat, acetaminophen, cyclophosphamide and 5-fluorouracil.

12. The method of claim 8 wherein said glutamine is administered parenterally.

13. The method of claim 12 wherein said glutamine is administered intravenously.

14. The method of claim 8 wherein said glutamine is administered enterally.

15. A method of treating drug overdose in a mammal, wherein said drug or a metabolite thereof comprises a nucleophilic reactive group and said drug overdose results in a diminished glutathione level, said method comprising administering to a mammal in need of said treatment an amount of glutamine, said amount being effective to enhance and maintain the hepatic glutathione levels.

16. The method of claim 15 wherein said drug is acetaminophen.

17. The method of claim 15 wherein said mammal is a human.

18. The method of claim 15 wherein said glutamine is administered parenterally.

19. The method of claim 18 wherein said glutamine is administered intravenously.

20. The method of claim 15 wherein said glutamine is administered enterally.

21. A method of reducing radiation-induced oxidative damage to a tissue in a mammal suffering from reduced glutathione levels as the result of radiation, said method comprising administering to said mammal an amount of glutamine, said amount being effective to enhance and maintain tissue glutathione levels.

22. The method of claim 21 wherein said radiation is X-irradiation.

23. The method of claim 21 wherein said mammal is a human.

24. The method of claim 21 wherein said glutamine is administered parenterally.

25. The method of claim 24 wherein said glutamine is administered intravenously.

26. The method of claim 21 wherein said glutamine is administered enterally.

* * * * *